(12) United States Patent
Shimizu et al.

(10) Patent No.: US 9,987,026 B2
(45) Date of Patent: Jun. 5, 2018

(54) MEDICAL INSTRUMENT

(71) Applicant: TERUMO KABUSHIKI KAISHA, Shibuya-ku, Tokyo (JP)

(72) Inventors: Katsuhiko Shimizu, Fujinomiya (JP); Youichirou Kuwano, Atsugi (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days. days.

(21) Appl. No.: 14/821,237

(22) Filed: Aug. 7, 2015

(65) Prior Publication Data

US 2015/0342625 A1 Dec. 3, 2015

Related U.S. Application Data

(63) Continuation of application No. PCT/JP2013/053153, filed on Feb. 8, 2013.

(51) Int. Cl.
| | |
|---|---|
| *A61B 17/22* | (2006.01) |
| *A61N 7/02* | (2006.01) |
| *A61B 18/00* | (2006.01) |
| *A61N 7/00* | (2006.01) |

(52) U.S. Cl.
CPC .......... *A61B 17/2202* (2013.01); *A61N 7/022* (2013.01); *A61B 2018/00541* (2013.01); *A61N 2007/0078* (2013.01)

(58) Field of Classification Search
CPC ............ A61N 7/022; A61N 2007/0078; A61B 17/2202; A61B 2018/00541
See application file for complete search history.

(56) References Cited

U.S. PATENT DOCUMENTS

| | | | | |
|---|---|---|---|---|
| 4,777,951 | A * | 10/1988 | Cribier | A61M 25/0023 600/485 |
| 5,295,995 | A * | 3/1994 | Kleiman | A61M 25/104 604/103.07 |
| 5,618,275 | A * | 4/1997 | Bock | A61B 17/20 601/2 |
| 6,491,711 | B1 * | 12/2002 | Durcan | A61M 25/1038 606/194 |
| 6,852,097 | B1 * | 2/2005 | Fulton, III | A61B 17/22012 604/266 |
| 2001/0025187 | A1 | 9/2001 | Okada | |
| 2003/0125620 | A1 | 7/2003 | Satou et al. | |

(Continued)

FOREIGN PATENT DOCUMENTS

| | | | |
|---|---|---|---|
| EP | 2 065 002 A1 | 6/2009 | |
| EP | 2065002 A1 * | 6/2009 | ....... A61B 17/22012 |

(Continued)

*Primary Examiner* — Richard Louis
(74) *Attorney, Agent, or Firm* — Buchanan Ingersoll & Rooney PC

(57) ABSTRACT

A medical instrument is disclosed for crushing a thrombus present in a pulmonary artery of a living body by an ultrasonic vibration. The medical instrument includes an elongated main body section capable of being inserted into an airway of the living body, and an ultrasonic oscillation section which can be inserted into the living body by the main body section and which oscillates the ultrasonic vibration inside the living body. By the medical instrument, a thrombus present in a pulmonary artery can be rapidly crushed, whereby a therapeutic effect on pulmonary embolism can be obtained.

6 Claims, 15 Drawing Sheets

(56) References Cited

U.S. PATENT DOCUMENTS

2003/0229370 A1* 12/2003 Miller ............ A61B 17/320725
 606/159
2005/0021065 A1* 1/2005 Yamada ............ A61B 17/32002
 606/169

FOREIGN PATENT DOCUMENTS

| JP | 63-305856 A | 12/1988 |
|---|---|---|
| JP | 4-307054 A | 10/1992 |
| JP | 2001-259025 A | 9/2001 |
| JP | 2003-24442 A | 1/2003 |
| JP | 2003-190180 A | 7/2003 |
| JP | 2010-509032 A | 3/2010 |
| JP | 2011-510933 A | 4/2011 |
| WO | WO 2008-061152 A2 | 5/2008 |
| WO | WO 2009/094718 A1 | 8/2009 |

* cited by examiner

MEDICAL INSTRUMENT

CROSS-REFERENCES TO RELATED APPLICATIONS

This application is a continuation of International Application No. PCT/JP2013/053153 filed on Feb. 8, 2013, the entire content of which is incorporated herein by reference.

TECHNICAL FIELD

The present disclosure relates to a medical instrument for crushing a thrombus present in a pulmonary artery by ultrasonic vibration.

BACKGROUND DISCUSSION

There has been known pulmonary embolism in which a thrombus formed in a vein in a lower limb or the like is moved by a bloodstream into a pulmonary artery and the bloodstream in the pulmonary artery is inhibited by the thrombus. As a treating method for the pulmonary embolism, conventionally, there has been adopted a method of administering a drug such as an anticoagulant and a thrombolytic agent (see Japanese Translations of PCT for Patent No. 2011-510933), or a method of implanting a thrombus filter or the like at the stage of confirmation of the presence of a thrombus in a vein in a lower limb (see Japanese Patent Laid-Open No. 2001-259025).

However, the therapeutic method of using a drug can be disadvantageous in that it can take time for the effect of the administered drug to appear. According to the method of using a thrombus filter, for example, it can be necessary to accurately grasp the position where the thrombus is present, prior to the onset of pulmonary embolism. By these methods, therefore, it may be impossible to adequately cope with a serious emergency patient abruptly suffering pulmonary embolism, and, depending on the patient's condition, it may be impossible to produce a substantial therapeutic effect.

Accordingly, a medical instrument is disclosed which can speedily crush a thrombus present in a pulmonary artery and thereby can obtain a substantial therapeutic effect on pulmonary embolism.

SUMMARY

A medical instrument is disclosed for crushing a thrombus present in a pulmonary artery of a living body by an ultrasonic vibration, which can include an elongated main body section capable of being inserted into an airway of the living body. The medical instrument can also include an ultrasonic oscillation section which can be inserted into the living body by the main body section and which oscillates the ultrasonic vibration inside the living body.

By oscillating the ultrasonic vibration from the airway located close to the pulmonary artery, the thrombus present in the pulmonary artery can be rapidly crushed. Therefore, a more positive therapeutic effect on pulmonary embolism can be obtained, as compared with the conventional treating methods based on the use of only a drug or a thrombus filter.

The medical instrument may further include a retaining section adapted to retain the ultrasonic oscillation section in relation to an inner wall of the airway.

According to this configuration, the ultrasonic vibration can be oscillated in a condition where the ultrasonic oscillation section is retained in relation to the inner wall of the airway. Therefore, the attenuation of the ultrasonic vibration within the airway can be suppressed, and thereby to favorably apply the ultrasonic vibration to the thrombus present in the pulmonary artery.

In the medical instrument, preferably, the retaining section has an expansion member expanded by injection of a fluid into the expansion member and contracted by discharge of the fluid from the expansion member, the main body section having a lumen which communicates with an inside of the expansion member and through which a fluid can flow, and the ultrasonic oscillation section is disposed on at least one of an outer surface of the expansion member and the inside of the expansion member.

According to this configuration, the expansion amount of the expansion member can be controlled according to the patient-dependent airway size, and thereby to reliably retain the ultrasonic oscillation section in relation to the airway. In addition, it is possible, by using a liquid as the fluid for expanding the expansion member, to apply the ultrasonic vibration through the liquid to the living body. Consequently, the ultrasonic vibration can be suitably applied to the thrombus present in the pulmonary artery.

In the medical instrument, preferably, the expansion member in its expanded state has an external shape formed with a recess such that a gap through which a fluid can flow is defined between the expansion member and the airway.

According to this configuration, in the condition where the expansion member is expanded, a fluid can be made to flow between the airway and the outer surface of the expansion member. Therefore, a flow of air through the airway can be ensured during the treatment for crushing the thrombus.

In the medical instrument, preferably, the ultrasonic oscillation section is disposed at a part on a distal end of the main body section, and the retaining section has a pressing member which extends from the main body section and which presses the ultrasonic oscillation section against the airway to thereby retain the ultrasonic oscillation section.

According to this configuration, the pressing member extended from the main body section makes it possible to press the ultrasonic oscillation section against the airway and thereby to retain the ultrasonic oscillation section in situ. Therefore, the ultrasonic vibration can be favorably applied to the thrombus present in the pulmonary artery. In addition, since a simply configured member such as the pressing member can be used, the configuration of the medical instrument can be prevented from being complicated due to the arrangement of the retaining section.

In the medical instrument, preferably, a plurality of the ultrasonic oscillation sections are disposed in different positions along a circumferential direction of the main body section, and the ultrasonic oscillation sections are capable of oscillating ultrasonic vibrations at different vibration frequencies.

According to this configuration, the ultrasonic vibrations can be oscillated radially from the airway, so that the ultrasonic vibrations can be applied over a wider range of the pulmonary artery. In addition, since the ultrasonic vibrations at different vibration frequencies can be oscillated respectively from the ultrasonic oscillation sections arranged in plurality, the thrombus can be reliably crushed, irrespectively of the magnitude of distance from the airway to the thrombus.

In the medical instrument, the ultrasonic oscillation section may have a transmission member adapted to transmit the ultrasonic vibration in a longitudinal direction of the main body section.

According to this configuration, since the ultrasonic vibration can be transmitted by the transmission member in the longitudinal direction of the main body section, the ultrasonic vibration can be oscillated from an arbitrary position in the longitudinal direction of the main body section. In addition, since the main body section itself can be put into an ultrasonic vibration, the main body section and various component members attached to the main body section can be made to function as the ultrasonic oscillation section.

In the medical instrument, preferably, the transmission member has an elongated metallic member wound around the main body section.

According to this configuration, the ultrasonic vibration can be favorably transmitted through the metallic member wound around the main body section.

The medical instrument may further include a rotational drive source driving a rotational motion of the ultrasonic oscillation section.

According to this configuration, the ultrasonic vibration can be oscillated while rotating the ultrasonic oscillation section. Therefore, the ultrasonic vibration can be oscillated radially from the airway. Consequently, the ultrasonic vibration can be applied over a wider range of the pulmonary artery.

In the medical instrument, preferably, an angle of beam spread of the ultrasonic vibration oscillated from the ultrasonic oscillation section can be controlled.

According to this configuration, since the angle of beam spread of the ultrasonic vibration oscillated from the ultrasonic oscillation section can be controlled, the angle of beam spread can be narrowed and the ultrasonic vibration can be applied in a converging manner. In addition, the angle of beam spread can be widened and the ultrasonic vibration can be applied over a wider range.

A medical instrument is disclosed for crushing a thrombus present in a pulmonary artery of a living body by an ultrasonic vibration, the medical instrument comprising: an elongated main body section configured to be inserted into an airway of the living body; and an ultrasonic oscillation section which can be inserted into the living body by the main body section and which oscillates the ultrasonic vibration inside the living body.

A medical instrument is disclosed for crushing a thrombus present in a pulmonary artery of a living body by an ultrasonic vibration, the medical instrument comprising: an elongated main body section configured to be inserted into an airway of the living body; an ultrasonic oscillation section which can be inserted into the living body by the main body section and which oscillates the ultrasonic vibration inside the living body; and a retaining section disposed on a distal end of the elongated main body section, the retaining section having an expansion member expanded by injection of a fluid into the expansion member and contracted by discharge of the fluid from the expansion member, and wherein the ultrasonic oscillation section is disposed on at least one of an outer surface of the expansion member and the inside of the expansion member.

A method is disclosed of crushing a thrombus in a pulmonary artery by ultrasonic vibrations, the method comprising: inserting a medical instrument into a living body, the medical instrument including an elongated main body section configured to be inserted into an airway of the living body and an ultrasonic oscillation section which is inserted into the living body by the main body section; and oscillating the ultrasonic vibrations from the ultrasonic oscillation section inside the living body.

DETAILED DESCRIPTION

Figure 1:
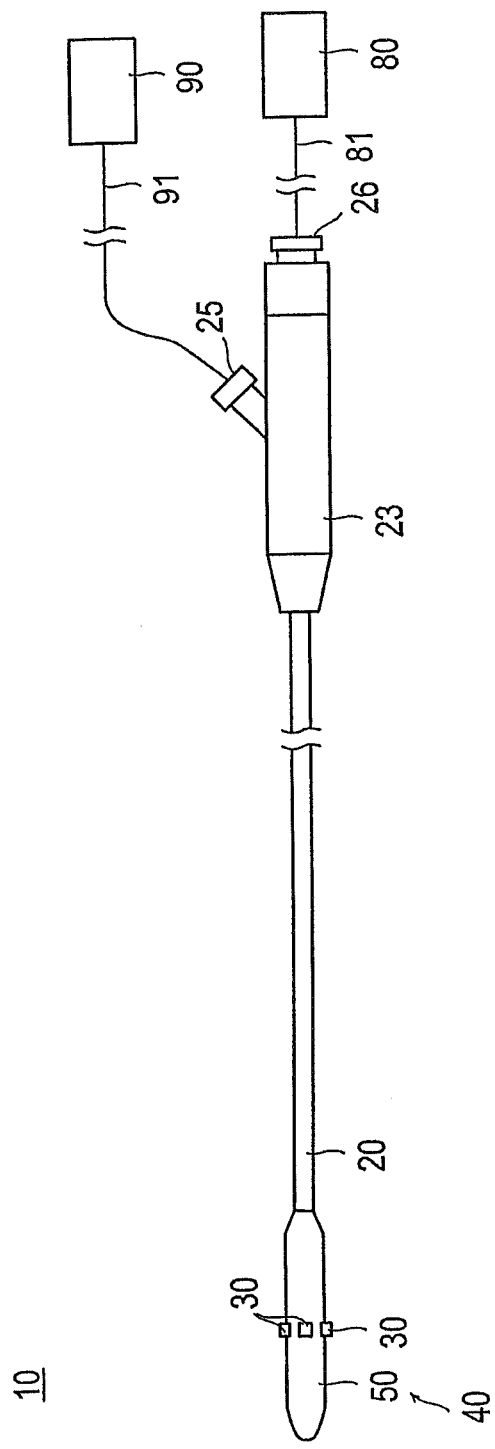
FIG. 1 illustrates schematically the general configuration of a medical instrument according to a first exemplary embodiment of the present disclosure.

Some embodiments of the present disclosure will be described below, referring to the drawings. Note that the dimensional ratios in the drawings are exaggerated for convenience of explanation and may therefore be different from the actual ratios.

First Embodiment

Figure 2A:
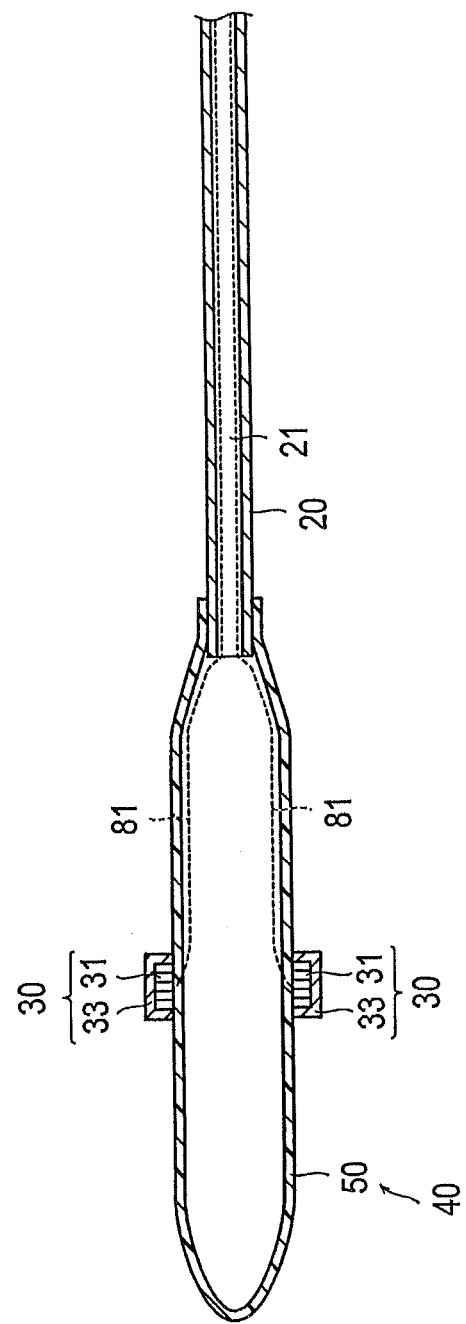
FIG. 2A is an enlarged sectional view of an expansion member provided in the medical instrument according to the first exemplary embodiment.
Figure 2B:
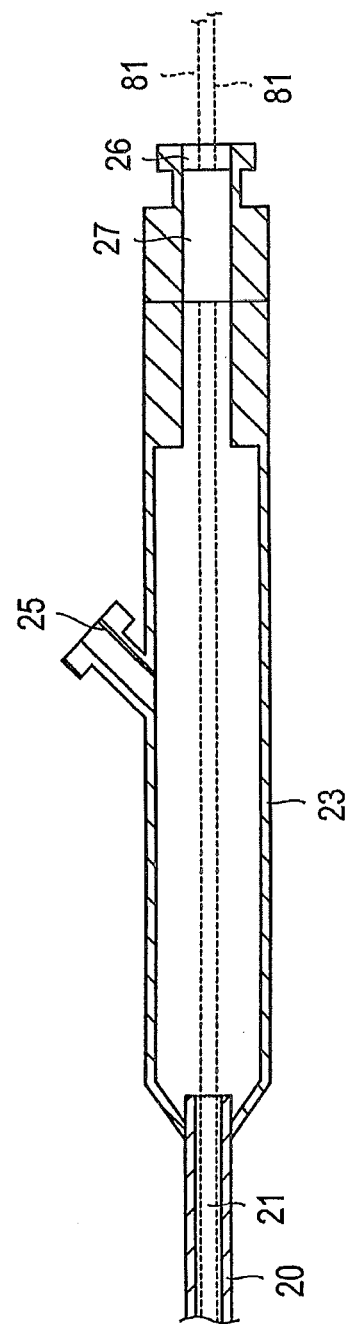
FIG. 2B is an enlarged sectional view of a hand operation section provided in the medical instrument according to the first exemplary embodiment.
Figure 3A:
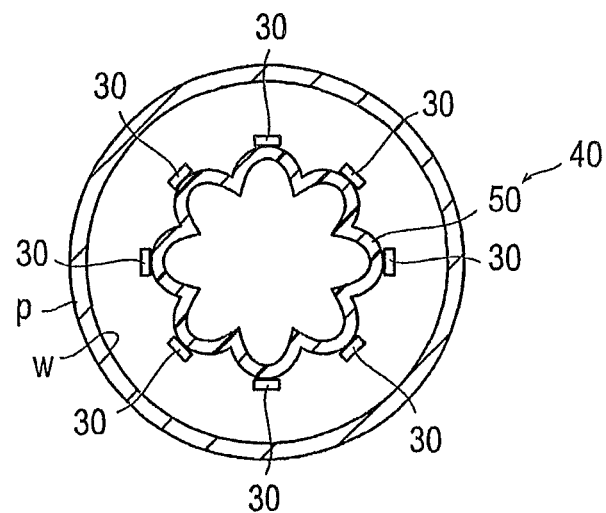
FIG. 3A is an enlarged sectional view showing the expansion member before expanded.
Figure 3B:
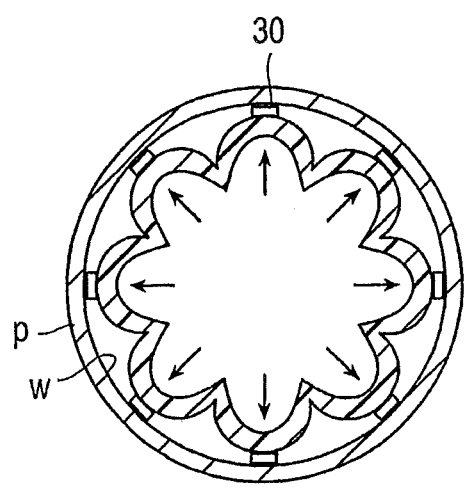
FIG. 3B is an enlarged sectional view showing the expansion member after expanded.
Figure 4:
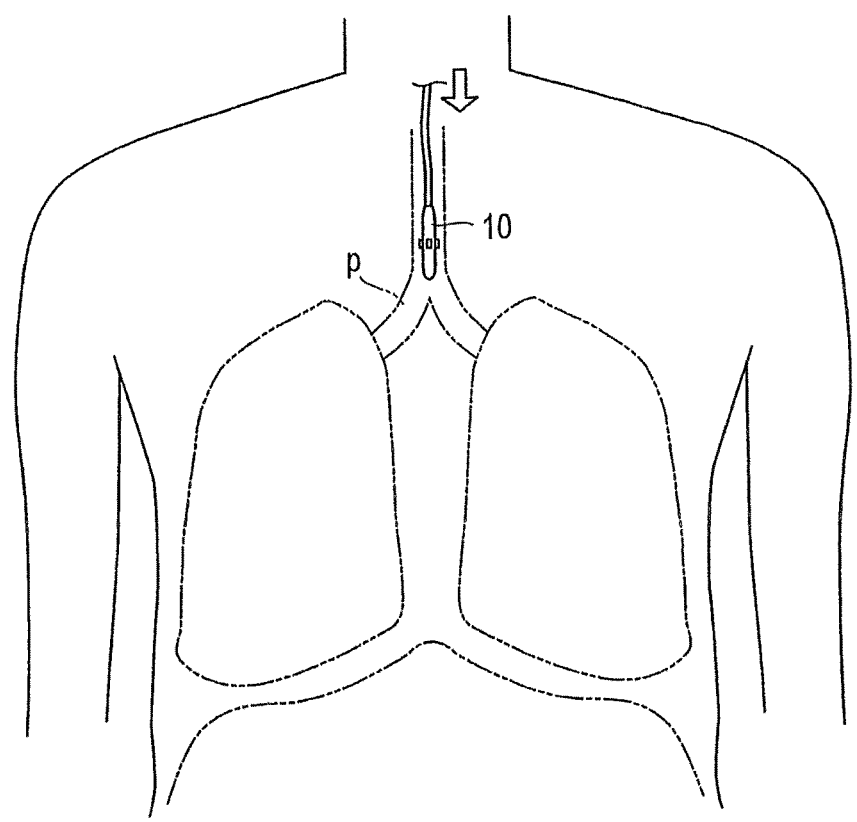
FIG. 4 is a schematic view for explaining an example of use of the medical instrument, showing a condition where the medical instrument has been introduced into an airway of a living body.
Figure 5A:
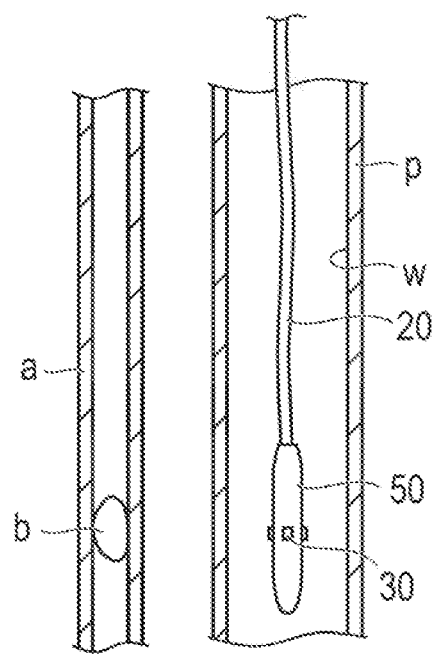
FIG. 5A is a sectional view for explaining an example of use of the medical instrument, showing schematically a state after the medical instrument is introduced into the airway of the living body and before an ultrasonic oscillator oscillates.
Figure 5B:
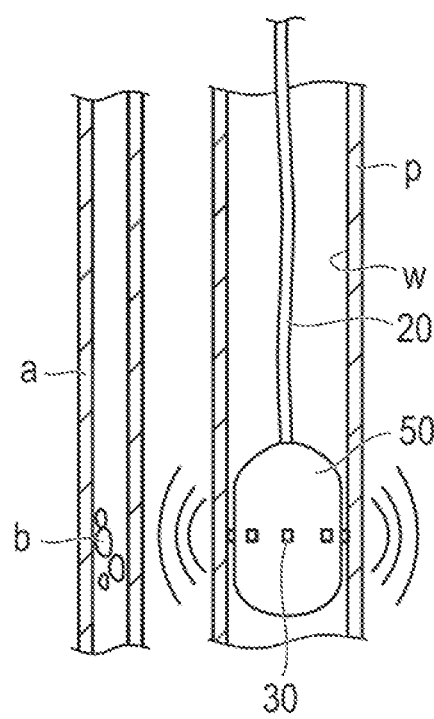
FIG. 5B is a sectional view for explaining an example of use of the medical instrument, showing schematically a state where an ultrasonic vibration is applied to a thrombus present in a pulmonary artery by the medical instrument introduced into the airway of the living body.

FIGS. 1 to 3 are views for explaining each component of a medical instrument according to an embodiment, which will be described by way of example, wherein FIGS. 2A and 2B show sectional views along the axial direction of the medical instrument, whereas FIGS. 3A and 3B show sectional views along a direction orthogonal to the axial direction of the medical instrument. FIGS. 4, 5A, and 5B are views for explaining examples of use of the medical instrument according to this embodiment.

As shown in FIGS. 1, 2A, and 2B, a medical instrument 10 according to this embodiment, can include an elongated main body section 20 which can be inserted in an airway of a living body, and an ultrasonic oscillation section 30 which can be introduced into the living body by the main body section 20 and which oscillates an ultrasonic vibration.

As illustrated in FIGS. 4, 5A, and 5B, the medical instrument 10 has a predetermined distal-end portion of the medical instrument 10 introduced into an airway (air tube, bronchial tube, bronchiole, terminal bronchiole, respiratory bronchiole, etc.) p perorally or transnasally. Then, an ultrasonic vibration is oscillated inside the airway p, and the ultrasonic vibration is applied to a thrombus b present inside a pulmonary artery a close to the airway p, whereby at least part of the thrombus b can be crushed (dissolved). Examples of the living body (patient) to be treated by use of the medical instrument 10 include a patient wherein a thrombus b formed in a deep vein of a lower limb is brought by a blood flow into a pulmonary artery a to cause pulmonary embolism, for example, a patient wherein part of the pulmonary artery a is clogged with the thrombus b to cause stagnation of blood and a rise in the right ventricular pressure of the heart so that there is a fear of angiorrhexis and an emergency treatment is needed. The examples of the living body (patient) to be treated are not limited to the just-mentioned, and include all the patients having a thrombus b generated in a pulmonary artery a for some reason.

Components of the medical instrument 10 according to this embodiment will be described.

As shown in FIG. 1, the medical instrument 10 can include the main body section 20 extended in an axial direction (in the left-right direction in the figure), a retaining section 40 disposed on a distal end of the main body section 20, ultrasonic oscillation sections 30 disposed on the retaining section 40, and a hand operation section 23 disposed on a proximal end of the main body section 20.

In using the medical instrument 10, a control section 80 for controlling the operation of the ultrasonic oscillation sections 30, a fluid supply section 90 for, for example, supplying a fluid to the medical instrument 10, and the like can be additionally used. As the control section 80, there can be used, for example, a central processing unit (CPU) in which an operation control program and the like are preliminarily incorporated. As the fluid supply section 90, there can be used, for example, a known fluid pump (syringe pump, etc.) which can send a fluid under pressure.

The main body section 20 may be formed of a rigid material or may be a flexible one formed of a flexible material, an elastic material or the like, so long as it can be introduced into a living body. Examples of the material usable for forming the main body section 20 can include various flexible or rigid resins such as polyvinyl chloride, polyethylene, polypropylene, cyclic polyolefins, polystyrene, poly(4-methylpentene-1), polycarbonate, acrylic resins, acrylonitrile-butadiene-styrene copolymer, polyesters such as polyethylene terephthalate, polyethylene naphthalate, etc., butadiene-styrene copolymer, and polyamides (for example, nylon 6, nylon 6.6, nylon 6.10, nylon 12); various rubber materials such as natural rubber, butyl rubber, isoprene rubber, butadiene rubber, styrene-butadiene rubber, silicone rubbers, etc.; various thermoplastic elastomers based on polyurethane, polyester, polyamide, olefin, styrene or the like; various metallic materials such as stainless steel, aluminum, copper and copper alloys; and various ceramics such as various glasses, alumina, silica, etc.

As shown in FIG. 2A, the ultrasonic oscillation section 30 can include a known piezoelectric element unit 31 including, for example, a piezoelectric element (omitted in the drawing) and electrode plates (omitted in the drawing) mounted on polarization surfaces on both sides of the piezoelectric element for the purpose of impressing a voltage on the piezoelectric element, and a housing 33 in which the piezoelectric element unit 31 is housed.

As the piezoelectric element, there can be used, for example, those which are formed from a piezoelectric ceramic such as barium titanate ($BaTiO_3$), lead zirconate titanate ($PB(Zi,Ti)O_3$), lithium niobate ($LiNbO_3$), and lithium tantalate ($LiTaO_3$). As the material constituting the housing 33, there can be used metallic materials, which can transmit ultrasonic vibrations to the outside of the housing 33 while suppressing attenuation, such as iron and titanium.

A plurality of the piezoelectric element units 31 are juxtaposedly arranged inside the housing 33. Though shown in a simplified form in the figure, the control section 80 transmits pulse signals individually to the piezoelectric element units 31 through signal lines 81, and can thereby control the operations of the piezoelectric element units 31 so that the piezoelectric element units 31 oscillate ultrasonic vibrations at different timings. A specific example of the control is a control wherein the pulse signal transmitted to each piezoelectric element unit 31 is provided with a delay time, and vibrators are driven sequentially so that the ultrasonic vibrations are radiated in a sector shape as a whole (the angle of beam spread of the ultrasonic vibration is widened). An example of the control is a control wherein, contrary to the above, the pulse signal is provided with a delay time, and the ultrasonic vibrations are radiated so that the vibrations are converged into a predetermined focal point (the angle of beam spread of the ultrasonic vibration is narrowed). Such types of control as just-mentioned are selectively applied according to the patient's condition, the plan of therapy, and the like.

For example, in the case where the position of the thrombus b present in the pulmonary artery a is not definite at the time of treatment, where the thrombi b are present in a plurality of places or where there is a long part which is peculiar to the pulmonary artery a and which is susceptible to clogging with a thrombus b, there is carried out a control for widening the angle of beam spread of ultrasonic vibration so that the ultrasonic vibration is radiated into a comparatively wide range. For example, in the case where the position of a thrombus b is preliminarily determined definitely before treatment or where a thrombus b is present only in one place, there is conducted a control for narrowing the angle of beam spread of ultrasonic vibration so that the ultrasonic vibration is applied locally. Note that the method for controlling the angle of beam spread of the ultrasonic vibration is not limited to the method of regulating the delays of the pulse signals, but may include a method wherein an acoustic lens is used and a method wherein a single-element probe (a probe having a single vibrator element for transmission and a single vibrator element for reception) is used.

In the medical instrument 10 according to this embodiment, a plurality of ultrasonic oscillation sections 30 can be disposed in different positions along the circumferential direction of the main body section 20. The number of the ultrasonic oscillation sections 30 to be disposed is not particularly limited; for example, eight ultrasonic oscillation sections 30 can be provided at regular intervals along the circumferential direction of the main body section 20 (see FIGS. 3A and 3B).

The ultrasonic oscillation sections 30 are so configured that they can oscillate ultrasonic vibrations at different vibration frequencies. The setting of the vibration frequency at which each of the ultrasonic oscillation sections 30 oscillates is performed, for example, by controlling a voltage to be impressed on the relevant piezoelectric element by the control section 80. It is sufficient for the vibration frequency of the ultrasonic vibration oscillated by each ultrasonic oscillation section 30 to be so set that at least part of a thrombus b in a pulmonary artery a can be crushed and thereby an increase in the flow rate of bloodstream can be realized; for example, the vibration frequency is set in the range of 500 kHz to 5 MHz. It is to be noted here, however, that the vibration frequency can be modified on a patient basis or a treatment run basis, since the vibration frequency should be appropriately controlled according to patient-basis individual differences in, for example, the distance from the airway to the pulmonary artery.

The retaining section 40 is provided for retaining the ultrasonic oscillation section 30 in relation to an inner wall w of the airway p at the time of using the medical instrument 10 (see FIG. 5B). Since the inside of the airway p is filled with air, which is a gas, when an ultrasonic vibration is oscillated within the airway p, the ultrasonic vibration may be attenuated and may fail to be transmitted to the thrombus b in the pulmonary artery a. In view of this, the ultrasonic oscillation section 30 is retained in the manner of being pressed against the airway p by the retaining section 40, whereby the ultrasonic vibration can be transmitted directly from the inner wall w of the airway p to the pulmonary artery a.

The retaining section 40 is composed of an expansion member 50, which is expanded by injection of a fluid into the expansion member 50 and is contracted by discharge of the fluid from the expansion member. In addition, the main body section 20 can include a lumen 21 which communicates with the inside of the expansion member 50 and through which a fluid can flow.

The hand operation section 23 disposed on the proximal end of the main body section 20 is provided with a port 25 to which a fluid tube 91 connected with a fluid supply section 90 can be connected in a liquid-tight and gas-tight fashion. Through the port 25, a fluid can be supplied into the lumen 21 of the main body section 20. In addition, the ultrasonic oscillation section 30 is disposed on an outer surface of the expansion member 50. Therefore, when the expansion member 50 is expanded within the airway p, the ultrasonic oscillation section 30 is pressed against the inner wall w of the airway p together with the outer surface of the expansion member 50, to be thereby retained in situ (see FIG. 3B).

The hand operation section 23 is provided with the port 25 for connection to the fluid tube 91, and with a port 26 through which the signal lines 81 connected to the piezoelectric elements are led out. In the vicinity of the port 26 through which to lead out the signal lines 81, there can be provided a seal member 27 for preventing the fluid for expanding the expansion member 50 from leaking out via the hand operation section 23. Note that also in positions where the signal lines 81 connected to the ultrasonic oscillation sections 30 disposed on the outer surface of the expansion member 50 are introduced to the inside of the expansion member 50, there can be provided a seal member or members or the like for preventing the fluid from leaking out of the expansion member 50. While the signal lines 81 may be laid to extend through the lumen 21 of the main body section 20 as shown in the drawings, they may also be laid to extend to the hand operation side in the state of, for example, being embedded in the main body section 20 or extending on the outside of the main body section 20.

A proximal portion of the expansion member 50 and a distal portion of the main body section 20 can be connected to each other by a known method such as adhesion or welding, taking into account the respective materials constituting them. A seal member may be provided for preventing the fluid from leaking via a joint portion between the expansion member 50 and the main body section 20.

As the material of the expansion member 50, there can be used materials similar to those for balloons used in balloon catheters known in the medical field. Examples of the material usable here include thermoplastic resins such as polyolefins such as polyethylene, polypropylene, ethylene-propylene copolymer, etc., polyesters such as polyethylene terephthalate, etc., polyvinyl chloride, ethylene-vinyl acetate copolymer, crosslinked-type ethylene-vinyl acetate copolymer, polyurethane, etc., polyamide elastomers, silicone rubbers, and latex rubber.

The fluid to be used for expansion of the expansion member 50 may be a gas or a liquid. A liquid is used as the fluid in the case where the ultrasonic oscillation sections 30 are disposed inside the expansion member 50, as in a modification, which will be described later. Examples of the liquid include physiological saline solution, while examples of the gas include helium gas, $CO_2$ gas, and $O_2$ gas.

As shown in FIGS. 3A and 3B, the expansion member 50 in its expanded state has an external shape formed with recesses 51 such that gaps through which a fluid can flow are defined between the expansion member 50 and the airway p. The expansion member 50 in this embodiment is formed with projections 53 together with the recesses 51, which are arrayed along the circumferential direction. When the expansion member 50 is expanded, the projections 53 come into contact with the inner wall w of the airway p, resulting in that a gap is defined between each of the recesses 51 and the airway p. The ultrasonic oscillation sections 30 are disposed on the projections 53, so that when the expansion member 50 is expanded the ultrasonic oscillation sections 30 are pressed against the inner wall w of the airway p by the projections 53. The gaps formed between the expansion member 50 and the airway p enable air to be circulated through the airway p even in the condition where the expansion member 50 is expanded. The numbers of the recesses 51 and the projections 53, the external shapes of the recesses 51 and the projections 53 and the like are not limited to those shown in the drawings but may be modified so long as a gap or gaps through which a fluid can flow are formed between the expansion member 50 and the airway p when the expansion member 50 is expanded.

A method of crushing a thrombus b in a pulmonary artery a by use of the medical instrument 10 according to this exemplary embodiment will now be described below.

First, utilizing a known imaging diagnostic apparatus such as a computed tomography (CT) apparatus, it is determined in which position of the pulmonary artery a the thrombus b is present. After the position of the thrombus b is determined, the medical instrument 10 is introduced into the living body, as shown in FIG. 4. The introduction into the living body can be carried out in the manner of pushing in a distal end of the medical instrument 10 into the airway p either perorally or transnasally. Note that in the case where an emergent treatment is needed, the operation of determining the object to be treated can be omitted, or an operation of determining the object to be treated by use of a predetermined imaging diagnostic apparatus can be carried out concurrently with the introduction of the medical instrument 10 into the living body.

Then, as shown in FIG. 5A, the ultrasonic oscillation sections 30 of the medical instrument 10 are positioned in the vicinity of the pulmonary artery a in which the thrombus b as the object to be treated is present. Thereafter, as shown in FIG. 5B, the expansion member 50 is expanded to press the ultrasonic oscillation sections 30 against the inner wall w of the airway p, thereby retaining the ultrasonic oscillation sections 30 in situ. In this condition, ultrasonic vibrations are oscillated from the ultrasonic oscillation sections 30, thereby crushing the thrombus b present in the pulmonary artery a. For example, the operation is conducted while checking the crushing of the thrombus b by use of a predetermined imaging diagnostic apparatus or the like, and the oscillation of the ultrasonic vibrations is stopped after the crushing is conducted sufficiently. Note that the crushing of the thrombus b may be conducted jointly using a known thrombolytic agent or the like with the medical instrument 10. By crushing the thrombus b by the medical instrument 10 and accelerating the dissolution of the thrombus b by the thrombolytic agent, the thrombus b can be removed at an enhanced efficiency. Examples of the thrombolytic agent usable here include streptokinase, anistreplase, urokinase (Abbokinase), tenecteplase, reteplase, tissue plasminogen activator (t-PA).

Thus, the method of crushing a thrombus present in a pulmonary artery by ultrasonic vibrations can include (i) a step of causing ultrasonic vibrations oscillated in the airway to act on the thrombus present in the pulmonary artery to crush at least part of the thrombus. In addition, the step (i) can include oscillating the ultrasonic vibrations from the ultrasonic oscillation sections in the condition where the ultrasonic oscillation sections are retained onto the inner wall of the airway. In addition, the step (i) can include expanding the expansion member so as to retain the ultrasonic oscillation sections onto the inner wall of the airway.

As a treating method for pulmonary embolism, there is a technique of treating the thrombus from the blood vessel side. However, with this approach, when a catheter is introduced up to that portion of a pulmonary artery a, which is clogged with the thrombus b, by way of the aorta, the catheter must be passed through the left ventricle, the left atrium, and the pulmonary vein. In addition, when the catheter is introduced to the target site by way of the cava, the catheter must be passed through the right atrium and the right ventricle. In either case, it takes time to introduce the catheter to the target site, notwithstanding the need of emergent treatment. Meanwhile, there is also a technique of treating a thrombus in a pulmonary artery by a shock wave applied from the exterior of the living body. In this case, however, other tissues serve as obstacles in application of the shock wave from the exterior of the body, the pulmonary artery is invisible, it can therefore be difficult to apply the shock wave to the target site to be treated, and there can be a risk of influencing the other tissues present between the pulmonary artery and the exterior of the body. In addition, where the ultrasonic oscillation sections 30 are disposed inside the airway p and operated to oscillate ultrasonic vibrations, the treatment from the airway p located close to the pulmonary artery a can be performed. Therefore, at least part of the thrombus b clogging the pulmonary artery a can be crushed by the ultrasonic vibrations to open a chink, whereby the pressure inside the pulmonary artery a can be relieved, and a shortening effect on treatment time can be obtained.

Thus, according to the medical instrument 10 in this embodiment, the ultrasonic vibrations are oscillated from the airway located close to the pulmonary artery, whereby the thrombus present in the pulmonary artery can be crushed speedily. Therefore, a more effective therapeutic effect on pulmonary embolism can be obtained, as compared with the conventional therapeutic methods based on the use of only a drug or a thrombus filter.

In addition, since the medical instrument 10 is configured to have the retaining section 40 for retaining the ultrasonic oscillation sections 30 onto the inner wall of the airway, attenuation of ultrasonic vibrations within the airway can be suppressed and thereby an adequate action of the ultrasonic vibrations on the thrombus present in the pulmonary artery can be realized.

In addition, the retaining section 40 has the expansion member 50 expanded by injection of a fluid into the expansion member 50 and contracted by discharge of the fluid from the expansion member 50, and the ultrasonic oscillation sections 30 are disposed on the outer surface of the expansion member 50. Therefore, the expansion amount of the expansion member 50 can be regulated in conformity with the airway size peculiar to the patient to be treated, and thereby, reliable retention of the ultrasonic oscillation sections 30 onto the airway can be realized.

The expansion member 50, in its expanded state, has an external shape formed with the recesses 51 such that the gaps through which a fluid can flow are defined between the expansion member 50 and the airway. Therefore, in the condition where the expansion member 50 is expanded, a fluid can flow between the airway and the outer surface of the expansion member 50, so that a flow of air through the airway can be ensured even during the treatment for crushing the thrombus.

The plurality of ultrasonic oscillation sections 30 can be disposed in different positions along the circumferential direction of the main body section 20, and the ultrasonic oscillation sections 30 can be configured to be able to oscillate ultrasonic vibrations at different vibration frequencies. Therefore, ultrasonic vibrations can be oscillated radially from the airway, so that the ultrasonic vibrations can be applied over a wider range of the pulmonary artery. In addition, since the ultrasonic vibrations at different vibration frequencies can be oscillated from the ultrasonic oscillation sections 30 arranged in plurality, the thrombus can be crushed reliably, irrespectively of the magnitude of distance from the airway to the thrombus.

Further, in the case where the angle of beam spread of the ultrasonic vibrations oscillated from the ultrasonic oscillation sections 30 can be controlled, the ultrasonic vibrations can converge by narrowing the angle of beam spread, and the ultrasonic vibrations can be applied over a wider range by widening the angle of beam spread.

A medical instrument 110 according to a modification of the first embodiment will be described below. The same members as those described in the first embodiment above are denoted by the same reference numerals as used above, and descriptions of them will be omitted.

Figure 6:
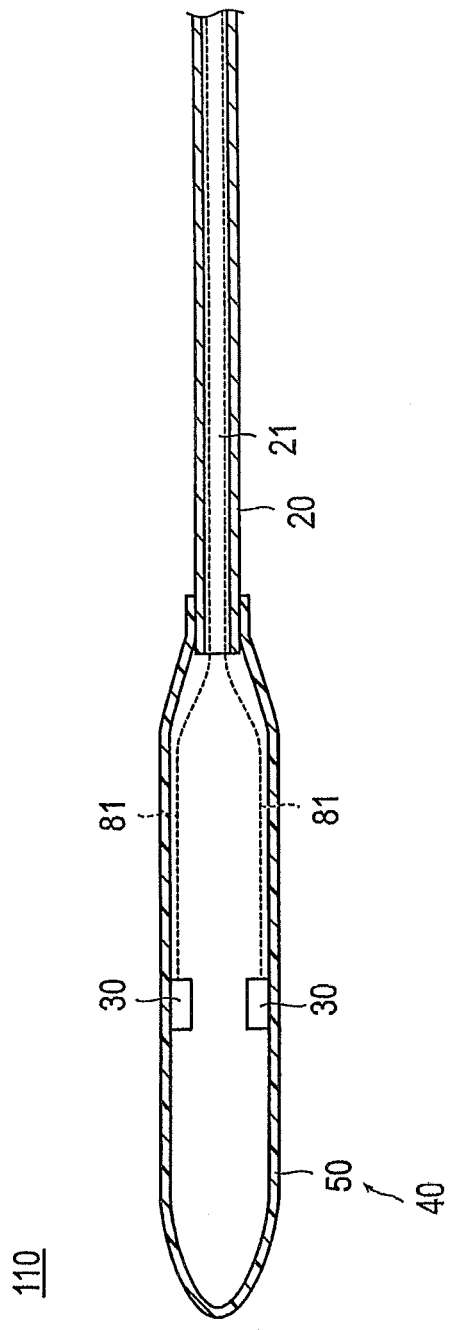
FIG. 6 is an enlarged sectional view of an expansion member provided in a medical instrument, for explaining a modification of the first exemplary embodiment.

While the ultrasonic oscillation sections 30 have been disposed on the outer surface of the expansion member 50 in the first embodiment described above, the ultrasonic oscillation sections 30 may be disposed, for example, in the inside of the expansion member 50 as depicted in FIG. 6. In such an arrangement, a liquid is used as the fluid for expanding the expansion member 50. When ultrasonic vibrations are oscillated from the ultrasonic oscillation sections 30 in the condition where the inside of the expansion member 50 is filled with the liquid, the ultrasonic vibrations are transmitted favorably through the liquid to the thrombus present in the pulmonary artery. In addition, by expanding the expansion member 50, the ultrasonic oscillation sections 30 disposed in the expansion member 50 can be retained in relation to the inner wall of the airway.

Thus, in a form wherein the expansion member 50 is used in the retaining section 40, the position in which to dispose the ultrasonic oscillation sections 30 may be on the outer surface of the expansion member 50 or in the inside of the expansion member 50, or may be both on the outer surface and in the inside. In any of these cases, the ultrasonic vibrations can be favorably applied to the thrombus present in the pulmonary artery.

A medical instrument according to a second exemplary embodiment of the present disclosure will be described below. The same members as those described in the first exemplary embodiment and modification above are denoted by the same reference numerals as used above, and descriptions of them will be omitted.

Figure 7:
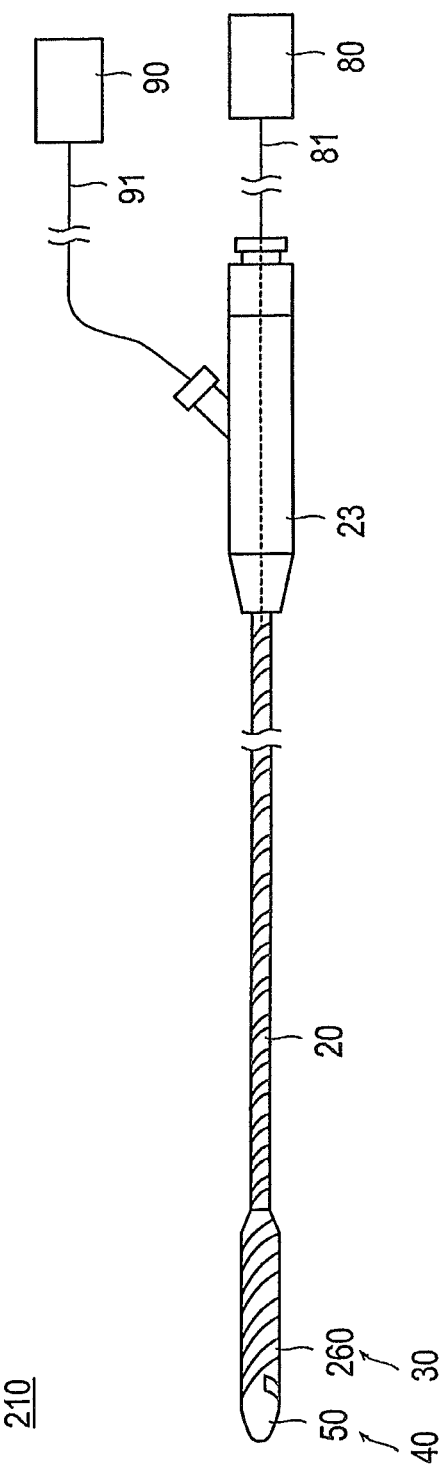
FIG. 7 illustrates schematically the general configuration of a medical instrument according to a second exemplary embodiment of the present disclosure.

In a medical instrument 210 according to this exemplary embodiment, as shown in FIG. 7, a transmission member 260 is provided which transmits ultrasonic vibration in the longitudinal direction of a main body section 20. The transmission member 260 not only has the function of transmitting the ultrasonic vibrations but also has a function as an ultrasonic oscillation section 30 for applying ultrasonic vibration to a living body. For example, the transmission member 260 is connected to an ultrasonic vibration unit 30 (omitted in the drawing) on the proximal end of the transmission member 260, and the ultrasonic vibration generated by the ultrasonic vibration unit 30 is transmitted through the transmission member 260 in the longitudinal direction of the main body section 20.

In addition, the transmission member 260 is composed of an elongated metallic member, which is wound around the whole part of the main body section 20 and, further, wound also around the outer surface of an expansion member 50 disposed at the distal end of the main body section 20, as shown in the drawing. With the transmission member 260 disposed in this way, the ultrasonic vibration generated on the proximal end of the main body section 20 can be efficiently transmitted to the distal end of the main body section 20.

At the time of crushing a thrombus present in a pulmonary artery, the expansion member 50 is expanded, whereon the transmission member 260 wound around the outer surface of the expansion member 50 is brought into close contact with the inner wall of an airway, thereby being maintained in situ. The ultrasonic vibration is oscillated from the portion of the close contact toward the pulmonary artery. For example, that portion of the transmission member 260, which is, wound around the expansion member 50 functions as the ultrasonic oscillation section 30. When the ultrasonic vibration is oscillated in such a form, a vibration of the expansion member 50 itself is also induced, so that trembling induced by the vibration of the expansion member 50 itself acts on the airway to tremble the airway as a whole, whereby a physical vibration can be applied to the thrombus present in the pulmonary artery. Consequently, the thrombus can be crushed more assuredly.

The material constituting the transmission member 260 is not particularly restricted so long as it can transmit ultrasonic vibrations. For efficient transmission of ultrasonic vibrations, however, a metallic material is used. As the metallic material, there is preferably used a material having a low internal damping factor, such as iron, stainless steel, aluminum, duralumin, titanium, and copper.

Thus, according to the medical instrument 210 in this exemplary embodiment, the ultrasonic vibration can be transmitted by the transmission member 260 in the longitudinal direction of the main body section 20, so that the ultrasonic vibration can be oscillated from an arbitrary position in the longitudinal direction of the main body section 20. In addition, since the main body section 20 itself can be put into an ultrasonic vibration, the main body section 20 and the component members attached to the main body section 20, such as the expansion member 50, can be made to function as the ultrasonic oscillation section 30. In addition, since the transmission member 260 is composed of a metallic member wound around the main body section 20, the ultrasonic vibration can be favorably transmitted through the transmission member 260.

A medical instrument according to a third exemplary embodiment of the present disclosure will be described. The same members as those described in the exemplary embodiments and modification above are denoted by the same reference numerals as used above, and descriptions of them will be omitted.

Figure 8:
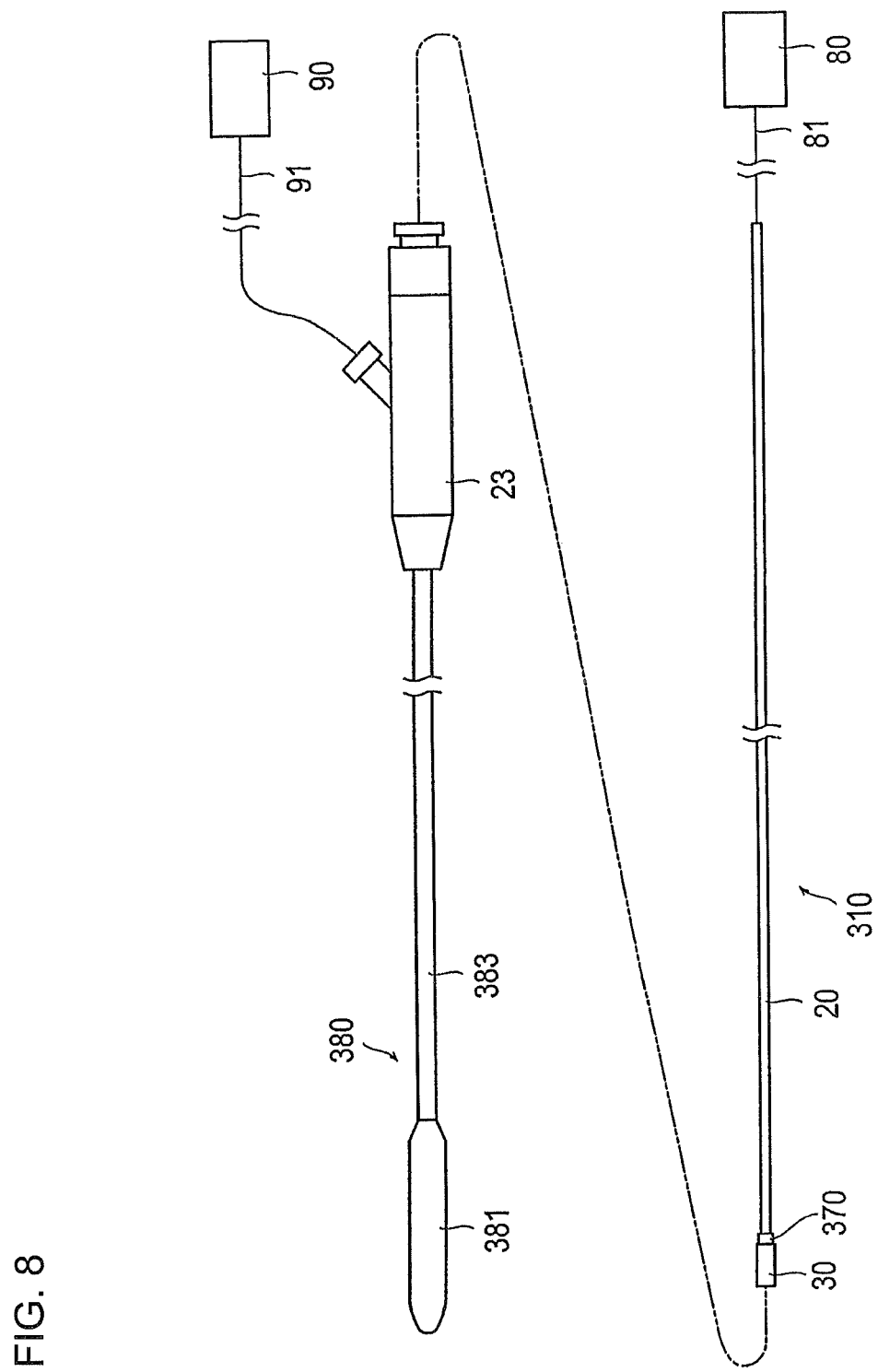
FIG. 8 illustrates schematically the general configuration of a medical instrument according to a third exemplary embodiment of the present disclosure.

As shown in FIG. 8, a medical instrument 310 according to this exemplary embodiment has a rotational drive source 370 for driving a rotational motion of an ultrasonic oscillation section 30. As the rotational drive source 370, there can be used a known one such as an electromagnetic motor, for example. The operation of the rotational drive source 370 can be controlled by a control section 80.

The medical instrument 310 can include an elongated main body section 20, and the ultrasonic oscillation section 30 disposed on a distal end of the main body section 20. In addition, in this embodiment, a catheter device 380 provided with an expansion member 381 is jointly used with the medical instrument 310. While the medical instrument and the expansion member have been integral with each other in the first and second exemplary embodiments above, the medical instrument 310 and the expansion member 381 can be configured as separate bodies in this exemplary embodiment. In addition, the medical instrument 310 can be inserted into and drawn out of the catheter device 380.

The expansion member 381 possessed by the catheter device 380 may be configured in the same manner as in the aforementioned exemplary embodiments. A main body section 383 possessed by the catheter device 380 and the main body section 20 possessed by the medical instrument 310 can be formed of the same or similar materials to the material for the main body section of the medical instrument in each of the aforementioned exemplary embodiments.

Figure 9A:
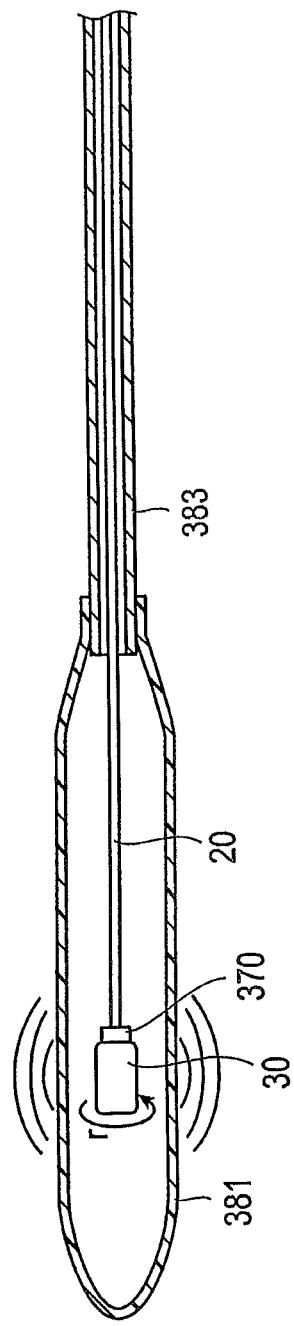
FIG. 9A is an enlarged sectional view of an expansion member provided in the medical instrument according to the third exemplary embodiment.
Figure 9B:
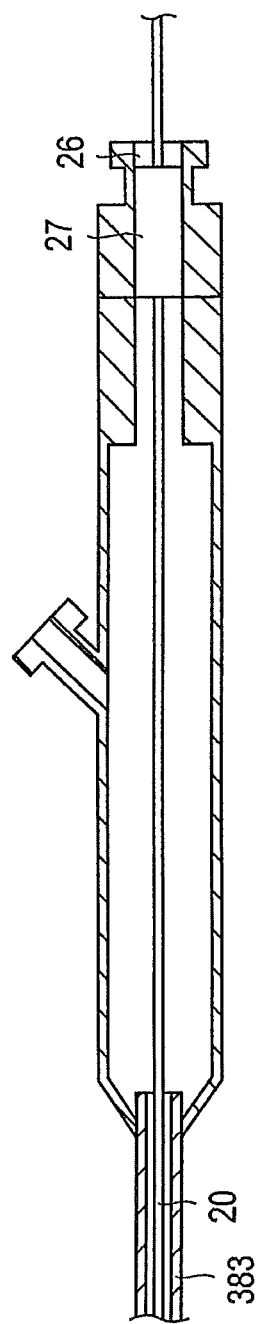
FIG. 9B is an enlarged sectional view of a hand operation section provided in the medical instrument according to the third exemplary embodiment.

A specific method for using the medical instrument 310 will be described. As shown in FIGS. 9A and 9B, the ultrasonic oscillation section 30 is inserted into the inside of the expansion member 381 via a port 26 of the catheter device 380. Then, in a condition where the inside of the expansion member 381 is filled with a liquid for expansion, an ultrasonic vibration is oscillated. The ultrasonic vibration oscillated from inside of the expansion member 381 is transmitted through the liquid, to be oscillated from the outer surface of the expansion member 381. Since the outer surface of the expansion member 381 is put in the state of being retained onto the inner wall of an airway, like in the aforementioned embodiments, the ultrasonic vibration can be oscillated from the outer surface toward a thrombus present in a pulmonary artery. While the ultrasonic vibration is being generated, the ultrasonic oscillation section 30 is rotated (arrow r in FIG. 9A indicates the rotation). With the ultrasonic oscillation section 30 thus put into a rotational motion, the ultrasonic vibration can be oscillated radially. Therefore, according to the medical instrument 310 in this exemplary embodiment, the ultrasonic vibration can be applied over a wider range of the pulmonary artery, whereby the thrombus present in the pulmonary artery can be crushed more reliably.

A medical instrument according to a fourth exemplary embodiment of the present disclosure will be described. The same members as those described in the aforementioned embodiments and modification are denoted by the same reference numerals as used above, and descriptions of them will be omitted.

Figure 10:
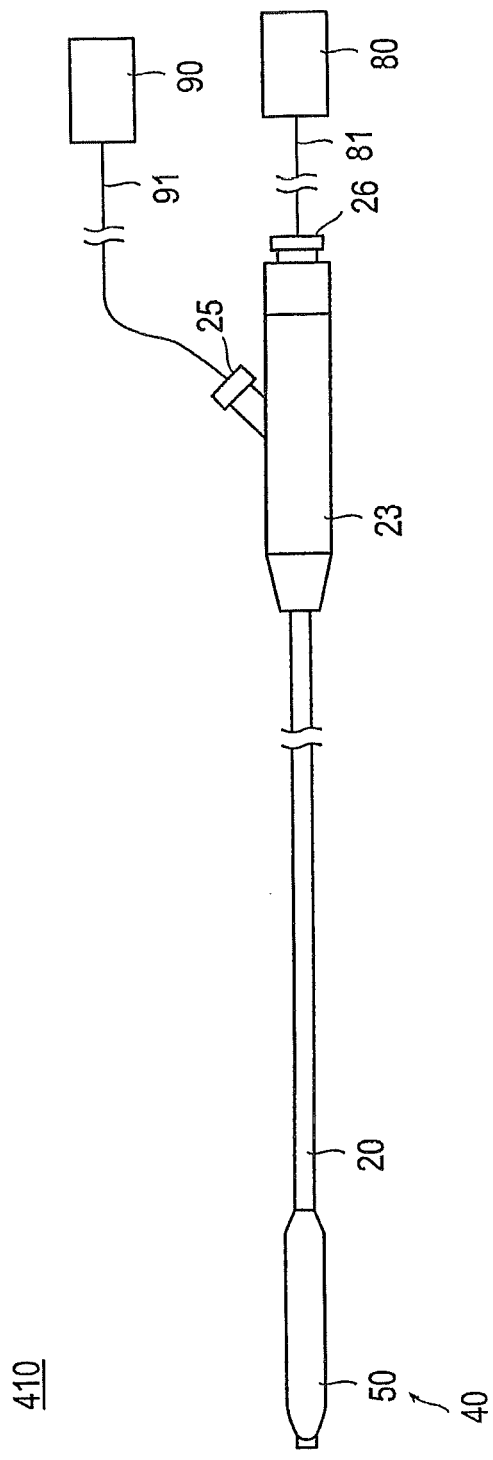
FIG. 10 illustrates schematically the general configuration of a medical instrument according to a fourth exemplary embodiment of the present disclosure.
Figure 11A:
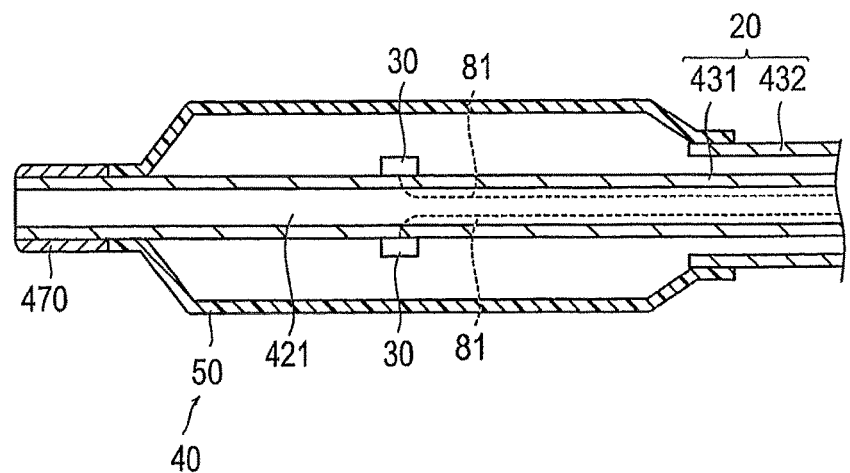
FIG. 11A is an enlarged sectional view of an expansion member provided in the medical instrument according to the fourth exemplary embodiment.
Figure 11B:
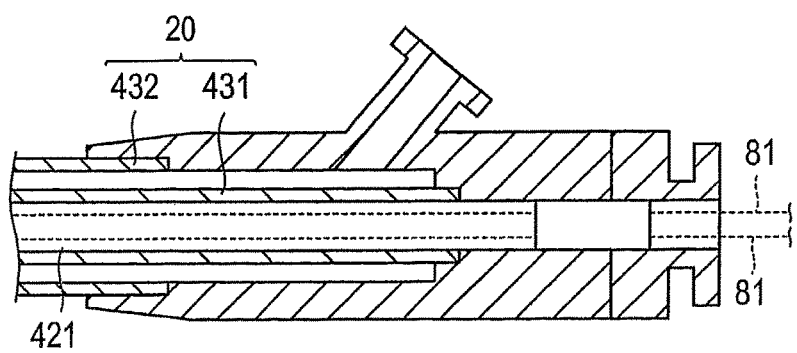
FIG. 11B is an enlarged sectional view of a hand operation section provided in the medical instrument according to the fourth exemplary embodiment.

As shown in FIGS. 10, 11A, and 11B, a medical instrument 410 according to this exemplary embodiment is configured as a so-called over-the-wire type catheter device. The medical instrument 410 is the same as the medical instrument 10 of the first exemplary embodiment in main configuration, but is different from the medical instrument 10 of the first exemplary embodiment in that the medical instrument 410 has a guide wire insertion lumen 421 which penetrates a main body section 20 and an expansion member 50.

The main body section 20 can be composed of an inner tube 431 and an outer tube 432, which can be possessed by an ordinary over-the-wire type catheter device. Each of the inner tube 431 and the outer tube 432 may be formed from the same or similar material to the material for the main body section 20 possessed by the medical instrument 10 according to the first embodiment. In addition, a tip 470 or the like may be provided, in the same manner as in the known balloon catheters. The other points of configuration of the medical instrument 410 according to this exemplary embodiment and the using method therefor are the same as those of the medical instrument 10 according to the first exemplary embodiment, and, therefore, detailed descriptions of them are omitted here.

A medical instrument according to a fifth exemplary embodiment of the present disclosure will be described. The same members as those described in the aforementioned embodiments and modification are denoted by the same reference numerals as used above, and descriptions of them will be omitted.

Figure 12A:
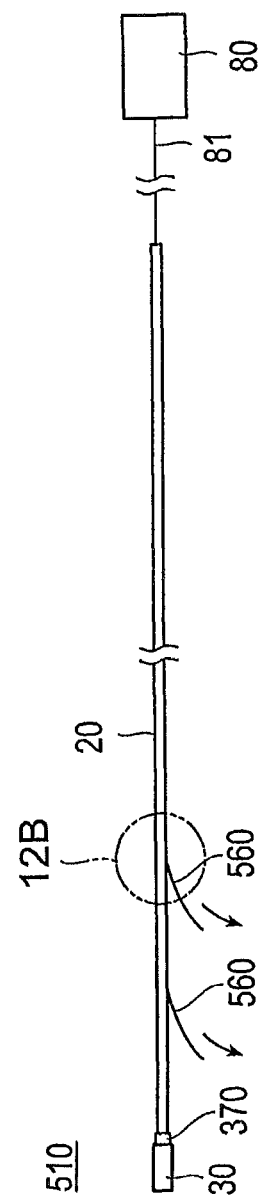
FIG. 12A illustrates schematically the general configuration of a medical instrument according to a fifth exemplary embodiment of the present disclosure.
Figure 12B:
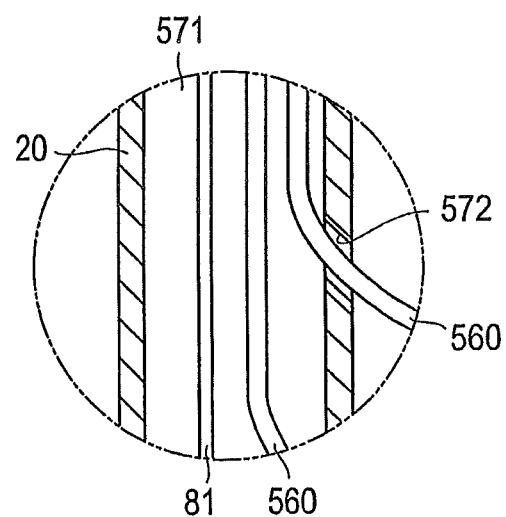
FIG. 12B is an enlarged sectional view of a part indicated by alternate long and two short dashes line 12B in FIG. 12A.

A medical instrument 510 according to this exemplary embodiment differs from the medical instruments according to the aforementioned exemplary embodiments in the configuration of a retaining section. As depicted in FIGS. 12A and 12B, the retaining section in this embodiment is composed of pressing members 560, which extend from a main body section 20 and press an ultrasonic oscillation section 30 against an airway, thereby retaining the ultrasonic oscillation section 30 in situ. Note that the total configuration of the medical instrument 510 is the same as those of the medical instrument 310 described in the third exemplary embodiment, and the medical instrument 510 can include the elongated main body section 20, the ultrasonic oscillation section 30 disposed on a distal end of the main body section 20, and a rotational drive source 370 for driving the ultrasonic oscillation section 30 to rotate.

The main body section 20 can include a lumen 571 in which the pressing members 560 are insertable, and a through-hole 572 communicating with the lumen 571. The pressing member 560 has an elongated bar-like overall external shape, can be moved within the lumen 571 and can have a distal end of the pressing member 560 protruded from the through-hole 572, by an operation on a hand operation side. As the material constituting the pressing members 560, there can be used, for example, an elastic material such as a resin material and a metallic material, and a shape memory alloy so re-shaped as to protrude from the through-hole 572 while curving. In addition, the main body section 20 may be provided with a plurality of the through-holes 572, and the plurality of the pressing members 560 may be used in accordance with the through-holes 572. In addition, the pressing members 560 may not be protruded from the main body section 20 but may be attached to the outer surface of the main body section 20.

According to the medical instrument 510 in this exemplary embodiment, the ultrasonic oscillation section 30 can be pressed against the airway, and thereby retained in situ, by the pressing members 560 extended from the main body section 20. Since a simply configured member such as the pressing member 560 is used, the configuration of the medical instrument 510 can be prevented from being complicated due to the arrangement of the retaining section.

While the medical instrument according to the present disclosure has been described with reference to the embodiments and modification, the disclosure is not to be limited to these embodiments, and appropriate modifications are possible on the basis of the descriptions in the appended claims.

The detailed description above describes a medical instrument. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of crushing a thrombus in a pulmonary artery by ultrasonic vibrations, the method comprising:
   inserting a medical instrument into an airway of a living body, the medical instrument including an elongated main body section configured to be inserted into the airway of the living body, an expansion member, and an ultrasonic oscillation section;
   oscillating the ultrasonic vibrations from the ultrasonic oscillation section inside the airway of the living body; and
   trembling the airway with the expansion member to crush the thrombus in the pulmonary artery.

2. The method according to claim 1, comprising:
   at a same time with the oscillating step, trembling the airway with the expansion member.

3. The method according to claim 1, comprising:
   injecting a thrombolytic agent into the pulmonary artery.

4. A method of crushing a thrombus in a pulmonary artery by ultrasonic vibrations, the method comprising:
   inserting a medical instrument into an airway of a living body, the medical instrument including an elongated main body section configured to be inserted into the airway of the living body, an expansion member, and an ultrasonic oscillation section; and
   oscillating the ultrasonic vibrations from the ultrasonic oscillation section in the airway to the pulmonary artery close to the airway inside the living body to crush the thrombus in the pulmonary artery close to the airway.

5. The method according to claim 4, comprising:
   disposing the ultrasonic oscillation section on a surface of the expansion member.

6. The method according to claim 4, comprising:
   injecting a thrombolytic agent into the pulmonary artery.

* * * * *